(12) United States Patent  (10) Patent No.: US 8,292,846 B2
Sargeant et al.  (45) Date of Patent: Oct. 23, 2012

(54) APPLICATOR TIP

(75) Inventors: Timothy Sargeant, Guilford, CT (US);
Arpan Desai, Hamden, CT (US);
Joshua Stopek, Guilford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 12 days.

(21) Appl. No.: 12/914,085

(22) Filed: Oct. 28, 2010

(65) Prior Publication Data

US 2012/0109053 A1 May 3, 2012

(51) Int. Cl.
*A61M 37/00* (2006.01)
*A61M 5/24* (2006.01)
*A61M 5/28* (2006.01)
*A61M 5/00* (2006.01)
*A61M 5/31* (2006.01)

(52) U.S. Cl. .................... 604/87; 604/206; 604/240
(58) Field of Classification Search .............. 604/82–92, 604/181, 187, 191, 200, 201, 202, 203, 204, 604/205, 206, 240–245, 48, 93.01; 606/213, 606/214
See application file for complete search history.

(56) References Cited

U.S. PATENT DOCUMENTS

| 2,688,966 | A |   | 10/1951 | Huber |
|---|---|---|---|---|
| 3,767,085 | A | * | 10/1973 | Cannon et al. ................. 222/82 |
| 4,952,209 | A |   | 8/1990 | Mühlbauer |
| 5,172,807 | A | * | 12/1992 | Dragan et al. ................. 206/219 |
| 5,286,257 | A |   | 2/1994 | Fischer |
| 5,330,426 | A |   | 7/1994 | Kriesel et al. |
| 5,501,371 | A |   | 3/1996 | Schwartz-Feldman |
| 5,531,683 | A |   | 7/1996 | Kriesel et al. |
| 5,779,668 | A | * | 7/1998 | Grabenkort ................. 604/89 |
| 5,829,639 | A |   | 11/1998 | Horner et al. |
| 5,928,611 | A |   | 7/1999 | Leung |
| 5,954,236 | A |   | 9/1999 | Virnelson |
| 6,047,864 | A | * | 4/2000 | Winkler ................. 222/326 |
| 6,436,078 | B1 |   | 8/2002 | Svedman |
| 6,547,467 | B2 |   | 4/2003 | Quintero |
| 6,732,887 | B2 |   | 5/2004 | Bills |
| 6,802,822 | B1 | * | 10/2004 | Dodge ................. 604/82 |
| 7,329,235 | B2 |   | 2/2008 | Bertron et al. |
| 7,435,237 | B2 | * | 10/2008 | Tan ................. 604/187 |
| 2003/0044219 | A1 |   | 3/2003 | Quintero |
| 2004/0142301 | A1 |   | 7/2004 | Maissami |
| 2006/0122563 | A1 |   | 6/2006 | Ziv |
| 2007/0108235 | A1 |   | 5/2007 | Sogaro |
| 2008/0105580 | A1 |   | 5/2008 | Nentwick et al. |
| 2008/0306439 | A1 |   | 12/2008 | Nelson et al. |

* cited by examiner

*Primary Examiner* — Matthew F DeSanto

(57) ABSTRACT

An applicator tip for use with a fluid applicator includes a base configured for releasable engagement with a fluid applicator at a proximal end of the base. The base includes a chamber defined therein configured for retaining a mixing component therein. One or more penetrable members are disposed within the base to at least partially encloses the chamber to retain the mixing component therein. A shaft extends distally from the base and defines a longitudinal axis. The shaft has a lumen extending therethrough configured for passage of a fluid therethrough. Upon penetration of the penetrable member, fluid from the fluid applicator flows into the chamber such that the fluid and the mixing component form a mixture to be applied.

15 Claims, 4 Drawing Sheets

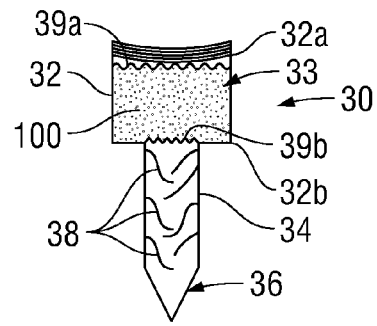
FIG. 3
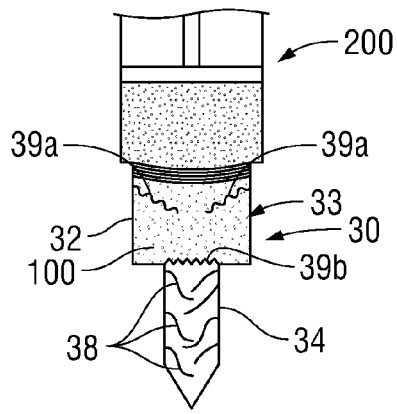 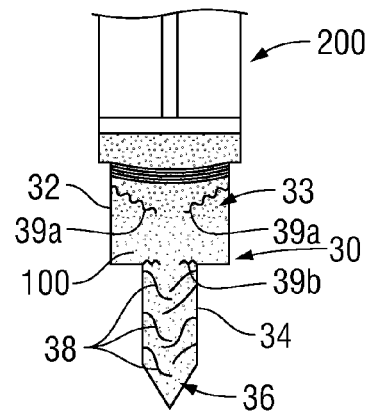
FIG. 4A  FIG. 4B
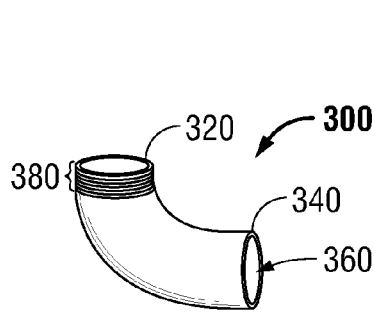 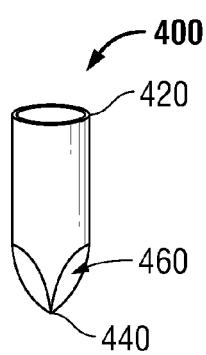 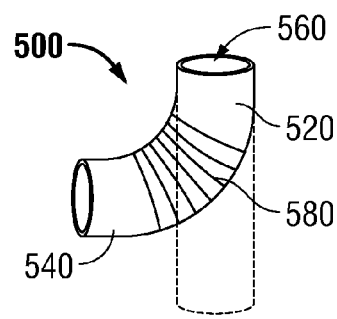
FIG. 5A  FIG. 5B  FIG. 5C

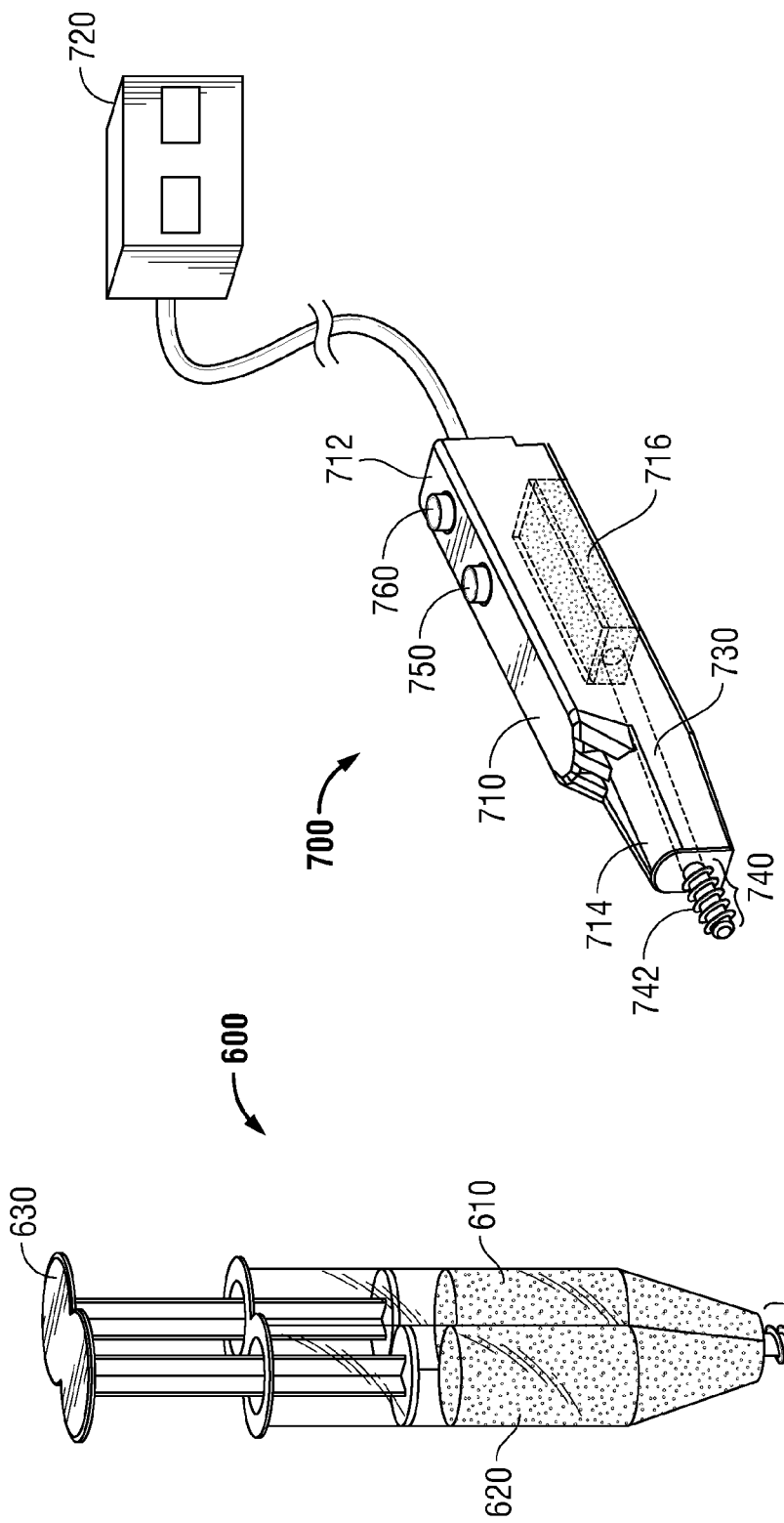

APPLICATOR TIP

BACKGROUND

1. Technical Field

The present disclosure relates to surgical instruments and, more particularly, to applicator tips configured and dimensioned for use with various fluid applicators.

2. Background of Related Art

Fluid applicators, e.g., syringes, are commonly used for injecting fluid mixtures such as drugs, nutrients, and the like, into the body. Typically, the clinician first prepares the fluid mixture by dissolving or mixing a dry component, e.g., drugs, nutrients, etc., into a carrier solution, or fluid component, e.g., saline solution. The fluid mixture is then loaded into the fluid applicator and delivered to the patient. However, while some mixtures may be prepared ahead of time, it is often advantageous, if not necessary, to mix the components immediately prior to use. Thus, in order to apply the mixture, the clinician must first take the additional steps of preparing the mixture and loading the fluid applicator with the prepared mixture.

SUMMARY

In accordance with the present disclosure, an applicator tip for use with a fluid applicator is provided. The applicator tip includes a base configured for releasable engagement with a fluid applicator. The base defines a chamber configured for retaining a mixing component therein. One or more penetrable members are disposed within the base for partially, or entirely, enclosing the chamber to retain the mixing component therein. A shaft defining a longitudinal axis extends distally from the base and has a lumen extending therethrough. The lumen of the shaft is configured for passage of a fluid therethrough. Upon penetration of the penetrable member(s), fluid from the fluid applicator flows into the chamber where the fluid and the mixing component mix to form a mixture to be applied, e.g., to a patient.

In one embodiment, the penetrable member(s) is penetrated upon engagement of the base to the fluid applicator. Alternatively, the penetrable member(s) may define a predetermined threshold such that when a force of fluid flow on the penetrable member(s) exceeds the predetermined threshold, the fluid penetrates the penetrable member.

In another embodiment, the base includes first and second penetrable members disposed at proximal and distal ends, respectively, of the chamber for sealing the mixing component within the chamber.

In another embodiment, the penetrable member(s) is a penetrable foil or other suitable penetrable material that seals the mixing component within the chamber. Further, the applicator tip may be pre-configured as an "off-the-shelf" applicator tip, i.e., where the mixing component is sealed within the chamber by the penetrable member(s) during manufacture.

The mixing component may be in the form of a powder, a coating, a foam, and/or an aerogel. The mixing component may also include a biologically active compound.

The fluid supplied to the base member (for mixing with the mixing component may be, for example, a saline solution, a pre-cursor to a hydrogel, a sealant, or an adhesive, although other fluids are contemplated.

The applicator tip may be disposable after a single use or, alternatively, may be reusable and sterilizable.

In yet another embodiment, a nozzle is disposed at a distal end of the shaft. The nozzle may be configured for applying the mixture in a desired direction and/or flow pattern. Further, the nozzle may be integral with the shaft or releasably engageable with the shaft.

In still yet another embodiment, the fluid supply assembly is one of manually and electrically actuated.

In another embodiment, the base is configured to threadingly engage the fluid applicator, although other engagement mechanisms are contemplated.

In yet another embodiment, one or more static mixers are disposed within the lumen of the shaft to facilitate mixing of the fluid and the mixing component. The static mixers may be coated with a mixing component or components.

BRIEF DESCRIPTION OF THE DRAWINGS

Various embodiments of the subject applicator tip are described herein with reference to the drawings wherein:

FIG. 3 is a side, cross-sectional view of another applicator tip in accordance with another embodiment of the present disclosure;

FIG. 4A is a side, cross-sectional view of the applicator tip of FIG. 3 shown in a first position;

FIG. 4B is a side, cross-sectional view of the applicator tip of FIG. 3 shown in a second position;

FIG. 5A is a side view of one embodiment of a nozzle for use with the applicator tip of FIG. 1 and FIG. 3;

FIG. 5B is a side view of another embodiment of a nozzle for use with the applicator tip of FIG. 1 and FIG. 3;

FIG. 5C is a side view of yet another embodiment of a nozzle for use with the applicator tip of FIG. 1 and FIG. 3;

FIG. 6 is a perspective view of a syringe configured for use with the applicator tip of FIG. 1 and FIG. 3;

FIG. 7 is a perspective view of an electrically powered fluid supply assembly configured for use with the applicator tip of FIG. 1 and FIG. 3;

DETAILED DESCRIPTION

Figure 1:
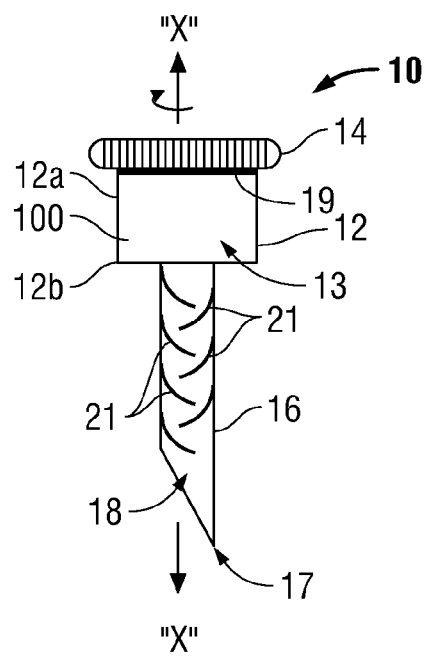
FIG. 1 is a side view of an applicator tip in accordance with one embodiment of the present disclosure.

Embodiments of the presently disclosed surgical instruments will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Turning now to FIG. 1, an applicator tip is shown generally designated by reference numeral 10. Applicator tip 10 includes a base portion 12 having a chamber 13 defined therein, a rotatable collar 14 disposed at proximal end 12a of base portion 12, and a shaft, or tubular portion 16 that extends distally from distal end 12b of base 12 and defines a longitudinal axis "X." Shaft 16 includes a lumen 18 extending therethrough. Lumen 18 is in fluid communication with chamber 13 defined within base portion 12. As shown in FIG. 1, shaft 16 defines a substantially linear configuration and includes a pointed or angled distal tip 17. However, as will be described in greater detail below, it is envisioned that shaft 16 define various configurations and/or that shaft 16 be configured to engage distal nozzles, e.g., nozzles 200, 300, 400 (see FIGS. 5A, 5B, 5B, respectively), of varying size, shape and/or configuration.

With continued reference to FIG. 1, rotatable collar 14 may include screw-fit threading (not explicitly shown) on an inner surface thereof, or may be otherwise configured for releasably securing applicator tip 10 to a fluid application device, e.g., fluid applicators 600, 700, 800 (see FIG. 6-8B). Collar 14 further defines an aperture 15 (see FIG. 2A) extending therethrough. As will be described in greater detail below, aperture 15 (see FIG. 2A) permits fluid to flow from the fluid application device, e.g., fluid applicators 600, 700, 800 (see FIG. 6-8B), into chamber 13 upon engagement of applicator tip 10 to the fluid application device.

Chamber 13 of base portion 12 of applicator tip 10 is configured to retain one or more mixing components 100 therein. In other words, applicator tip 10 is configured such that, upon passage of fluid through aperture 15 of collar 14 and into chamber 13 of base portion 12, the fluid mixes with the mixing component(s) 100 to form a mixture to be delivered to the patient. Applicator tip 10 may be pre-configured with a particular mixing component(s) 100 disposed within chamber 13. Thus, applicator tip 10 may be configured such that the user need only select the applicator tip 10 containing the desired mixing component(s) 100 and engage applicator tip 10 to a fluid application device, e.g., fluid applicators 600, 700, 800 (see FIG. 6-8B), in preparation for applying the fluid-mixing component mixture to the patient. Alternatively, applicator tip 10 may be configured such that the user may load chamber 13 with the desired mixing component(s) 100 prior to use. In such an embodiment, applicator tip 10 may be configured as a sterilizable, reusable applicator tip 10.

The mixing component(s) 100 may be in the form of a powder, foam, aerogel, semi-solid, solid, or any other form capable of dissolving, or mixing with a fluid for application to the patient. Specifically, the mixing component 100 may include pain drugs, oncological drugs (e.g., chemotherapy drugs), nutrients, vitamins, growth factors, genes, proteins, or other biologically active compounds. The mixing component 100 may also include compounds to form hydrogels, sealants, adhesives, or the like upon mixing with the fluid. The fluid supplied to chamber 13, i.e., the fluid to be mixed with the mixing component 100, may be water, saline solution, a precursor to a hydrogel, or any other suitable solution, gel, semi-solid, or paste.

The mixing component or components 100 may be sealed, or enclosed within chamber 13 with one or more penetrable or breakable barriers 19 configured to retain the mixing component(s) 100 within chamber 13 and to inhibit contamination of chamber 13 prior to use. More specifically, as shown in FIG. 1, proximal barrier 19 is disposed at proximal end 12a of base 12 to seal off chamber 13 from aperture 15 of collar 14 and, thus, from the fluid applicator device. It is also envisioned that additional barriers 19 be disposed within base 12, e.g., at distal end 12b of base 12. Further, the penetrable barriers 19 may be formed from a biocompatible foil, or other suitable material. As will be described in greater detail below, upon penetration of barrier(s) 19, communication is established between chamber 13 and the fluid applicator device and/or lumen 18 of shaft 16 such that fluid may flow therebetween.

Lumen 18 of shaft 16 may include one or more static mixing members 21 configured to promote mixing of the fluid and mixing component 100 upon passage through lumen 18. More particularly, static mixing members 21 may include metal or plastic panels arranged in a generally helical configuration. Such a configuration promotes mixing of the fluid and mixing component 100 by repeatedly diverting and altering the flow of the fluid and mixing component 100 through lumen 18. Alternatively, static mixing members 21 may be positioned in any other configuration and/or lumen 18 may include other features, e.g., dynamic mixing components (not shown), to promote mixing of the fluid and mixing components 100 during passage through lumen 18 of shaft 16. Static mixing member 21 may also include a mixing component, similar or different from mixing component 100, coated thereon for mixing with the fluid flowing through lumen 18 of shaft 16.

Figure 2A:
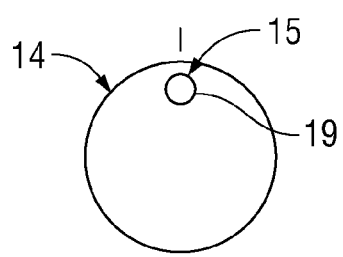
FIG. 2A is a top view of the applicator tip of FIG. 1 shown in a closed position.
Figure 2B:
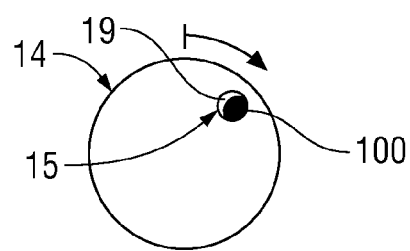
FIG. 2B is a top view of the applicator tip of FIG. 1 transitioning between the closed position and an open position.
Figure 2C:
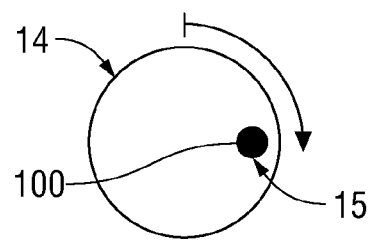
FIG. 2C is a top view of the applicator tip of FIG. 1 shown in an open position.

Turning now to FIGS. 2A-2C, in conjunction with FIG. 1, the use and operation of applicator tip 10 will be described. Initially, the desired applicator tip 10 selected, i.e., the applicator tip 10 including the desired mixing component 100 therein is selected. Alternatively, with respect to reusable applicator tips 10, the mixing component 100 is added to chamber 13 of base 12 and is sealed by one or more barriers 19. Next, the fluid applicator, e.g., syringe 600 (FIG. 6), is loaded with the desired fluid, e.g., saline solution. Applicator tip 10 is then engaged to syringe 600 by rotating rotatable collar 14 of applicator tip 10 with respect to syringe 600 (FIG. 6) such that rotatable collar 14 is threadingly engaged, or locked onto threading 642 of syringe 600 (FIG. 6).

Prior to engagement of rotatable collar 14 and syringe 600 (FIG. 6), as shown in FIG. 2A, barrier 19 occludes aperture 15, inhibiting fluid from passing therebetween, i.e., between syringe 600 and chamber 13 of base 12. Upon rotating collar 14 with respect to syringe 600 (FIG. 6) to engage applicator tip 10 thereon, as shown in FIG. 2B, foil barrier 19 is partially broken, or penetrated, e.g., by a barb or protrusion (not shown) extending distally from collar 14 or by the distal end 640 of syringe 600 (FIG. 6), allowing partial communication between syringe 600 (FIG. 6) and chamber 13 of base 12 via aperture 15. Upon further rotation of collar 14 with respect to syringe 600 (FIG. 6) into the fully engaged, or locked position, as shown in FIG. 2C, foil barrier 19 is penetrated to permit fluid communication between syringe 600 and chamber 13 of base 12. Accordingly, with applicator tip 10 engaged, or locked to syringe 600, fluid may be dispensed from syringe 600 (FIG. 6) into chamber 13 (via aperture 15 and the broken, or penetrated foil barrier 19) to mix with mixing component 100. Alternatively, collar 14 may be rotated with respect to base 12, as described above, to expose a perforated, or weakened portion of foil barrier 19 such that, when fluid is dispensed from syringe 600 (FIG. 6), the force of the fluid against barrier 19 breaks, or penetrates the perforated, or weakened portion of barrier 19 and enters chamber 13. Further, barrier 19 may define an opening or window (not shown) therein such that, upon alignment of aperture 15 and the window defined within barrier 19, i.e., upon the engagement of applicator tip 10 and syringe 600 (FIG. 6), fluid may communicate between syringe 600 and chamber 13 of base 12. As can be appreciated, further dispensing of the fluid, in any of the above-embodiments, urges the mixture through chamber 13, into lumen 18 of shaft 16 and, eventually, out distal tip 17 of shaft 16 for application to the patient.

With reference now to FIG. 3, another embodiment of an applicator tip, applicator tip 30 is shown. Applicator tip 30 is similar to applicator tip 10 (FIG. 1) and includes a base portion 32 and a shaft 34 extending distally from distal end 32b of base portion 32. Base portion 32 includes a chamber 33 defined therein and is configured to releasably engage a fluid application device, e.g., fluid applicators 600, 700, 800 (see FIG. 6-8B) via thread-lock engagement, snap-fit, friction fit, etc. Chamber 33 communicates with lumen 36 defined through shaft 34 such that fluid may be delivered from the fluid application device and through applicator tip 30 for application to the patient. Lumen 36 of shaft 34 may also include static mixing members 38 disposed therein to promote mixing of the fluid and mixing component upon passage through lumen 36, as discussed above with regard to applicator tip 10.

As in the embodiment discussed above, chamber 33 of base portion 32 may be configured to retain a mixing component 100 therein. More specifically, chamber 33 is sealed at a proximal end 32a of base 32 by a first penetrable barrier 39a, e.g., a foil barrier 39a, and at a distal end 32b of base 32 by a second penetrable foil barrier 39b. Accordingly, mixing component 100 is retained within chamber 33, inhibiting fluid and/or contaminates from entering chamber 33. As will be described below, upon dispensing of fluid from the fluid application device into applicator tip 30, when the force of the fluid against the penetrable barriers 39a, 39b reaches a predetermined threshold, barriers 39a and 39b are broken, or penetrated, to allow the fluid to flow into chamber 33, mix with the mixing component(s) 100, and enter lumen 36 of shaft 34.

Additionally, or alternatively, static mixing members 38 may include a mixing component or mixing components coated thereon for mixing with the fluid upon passage of the fluid through the lumen 36 of shaft 34. For example, the static mixing member 38 may be coated with a powder form of a bioactive agent, such that when fluids encounter the powdered bioactive agent, mixing occurs. Such a configuration may be desired, for example, where multiple mixing components are needed.

With reference now to FIGS. 4A and 4B, the use and operation of applicator tip 30 will be described. First, as in the previous embodiment, a desired applicator tip 30 is selected. Next, the applicator tip 30 is engaged to a fluid application device, e.g., fluid application device 200, via a thread-lock engagement, friction-fit, or the like. The fluid application device 200 is then moved into position such that the distal tip of shaft 34 of applicator tip 30 is positioned adjacent the area of application, i.e., the area where the mixture is to be applied.

At this point, the clinician may activate the fluid application device 200 to urge the fluid from the fluid application device 200 distally into applicator tip 30. As the fluid is urged toward first barrier 39a, the fluid exerts a force, or pressure on first barrier 39a. Once the pressure exerted on first barrier 39a exceeds the predetermined threshold of the barrier 39a, barrier 39a is broken, or penetrated, allowing the fluid to flow into chamber 33, as shown in FIG. 4A. As the fluid flows into chamber 33, it mixes with the mixing component 100. Eventually, as more fluid enters chamber 33, the force of the fluid against second barrier 39b exceeds the predetermined threshold of barrier 39b, at which point second barrier 39b is broken, or penetrated, allowing the fluid-mixing component mixture to flow into lumen 36 of shaft 34, as shown in FIG. 4B. The predetermined threshold of the second barrier 39b may be equal to or different from the predetermined threshold of the first barrier 39a and/or may be configured to allow for adequate mixing of the fluid and the mixing component 100 within chamber 33 prior to penetration of the second barrier 39b. Once the mixture enters lumen 36 of shaft 34, the mixture is mixed further by the static mixing members 38 disposed within lumen 36 of shaft 34, prior to application to the patient.

Turning now to FIGS. 5A-5C, various configurations of shafts, or nozzles for use with applicator tips 10, 30 (FIGS. 1 and 3, respectively) are shown. Nozzles 300, 400, 500 may be used in conjunction with, or in place of shafts 16, 34 of applicator tips 10, 30, respectively, to achieve the desired direction and/or form of fluid application.

Referring now to FIG. 5A, nozzle 300 is configured to engage distal end 12b of base 12 of applicator tip 10 (FIG. 1). It is also envisioned that nozzle 300 be configured to engage distal end 32b of base 32 of applicator tip 30 (FIG. 3). Nozzle 300 includes a proximal end 320, a distal end 340 and a lumen 360 extending therethrough. Nozzle 300 may include threading 380 at proximal end 320 thereof for releasably engaging distal end 12b of base 12 (FIG. 1) or may be configured to releasably engage base 12 (FIG. 1) via any other suitable mechanism, e.g., snap-fit, friction-fit, etc. Alternatively, nozzle 300 may be integral with, e.g., formed as a single component, with base 12 of applicator tip 12, similar to base 12 and shaft 16 shown in FIG. 1. As can be appreciated, when nozzle 300 is engaged to base 12 (FIG. 1), lumen 360 of nozzle 300 is in communication with chamber 33 such that, upon actuation, fluid may be urged through chamber 33 into lumen 360 of nozzle 300 for application to the body. As such, nozzle 300 may define a curved or arcuate configuration, as shown in FIG. 5A, to facilitate delivery of fluids to a particular location on or within the body. More specifically, the curved configuration may facilitate directing of fluids in remote areas within the body or difficult-to-reach areas on the body that are not readily accessible with a linear arrangement.

Nozzle 300 may be formed from any suitable rigid or semi-rigid medical grade material, e.g., stainless steel, or other suitable bio-compatible materials, e.g., polymeric materials. In some embodiments, nozzle 300 may be formed, at least partially, from a flexible material.

With reference now to FIG. 5B, another embodiment of a nozzle, nozzle 400, is shown including a proximal end 420 adapted to engage distal end 12b of base 12 (FIG. 1), a distal end 440 configured for application of fluids to or within the body, and a lumen 460 extending therethrough. More specifically, nozzle 400 defines a conically-shaped distal end 440 configured to facilitate mixing of fluids and/or application of fluids to the body. Nozzle 400 may otherwise be configured similar to nozzle 300 (FIG. 5A).

Referring now to FIG. 5C, yet another embodiment of a nozzle, nozzle 500, is shown including a proximal end 520 adapted to engage distal end 12b of base 12 (FIG. 1), a distal end 540 adapted to facilitate application of fluid to the body, and a lumen 560 extending therethrough. Nozzle 500 further includes an intermediate segment 580 disposed between proximal and distal ends 520, 540, respectively, thereof. Intermediate segment 580 of nozzle 500 is configured to permit articulation of distal end 540 of nozzle 500 with respect to proximal end 520 of nozzle 500 and, thus, with respect to longitudinal axis "X" when engaged to distal end 12b of base 12 (FIG. 1) in order to change the direction of application of fluid from nozzle 500. Intermediate segment 580 may be formed from a resilient flexible material such as rubber or a malleable metal, or, alternatively, may be formed from a shape memory material such as Nitinol. In one embodiment, intermediate section 580 defines a folded or accordion arrangement to permit flexing of the intermediate section 580 to arrange or direct the distal end 540 at a predetermined orientation.

Although several embodiments of nozzles are shown in FIGS. 5A-5C, it is envisioned that nozzles having various shapes, sizes and/or configurations may be provided for use with applicator tips 10, 30. Further, the nozzles, e.g., nozzles 300, 400, 500, may be interchangeable such that a specific nozzle may be selected according to the particular task to be performed. Additionally, nozzles 300, 400, 500 may be disposable, e.g., nozzles 300, 400, 500 may be discarded after a single use, or may be sterilizable for repeated use. Alternatively, as mentioned above, applicator tips 10, 30 may be integrally formed with one of nozzles 300, 400, 500 (or a nozzle of different configuration). In other words, shafts 16, 34 of applicator tips 10, 30, respectively, may be configured similar to any of the nozzles described above.

With reference now to FIG. 6, a syringe 600 is shown adapted for use with applicator tip 10 (FIG. 1). Syringe 600 includes two fluid chambers, or barrels 610, 620, for retaining fluids therein, although it is contemplated that syringe 600 include greater or fewer than two fluid chambers 610, 620. Syringe 600 further includes a manually-operable plunger 630 for urging fluid(s) from barrels 610, 620 through open distal end 640 of syringe 600. Distal end 640 of syringe 600 includes threading 642, e.g., screw-threading, or Luer threading, complementary to the threading of rotatable collar 14 of applicator tip 10 (FIG. 1) for releasably coupling distal end 640 of syringe 600 to proximal end 12a of base 12 of applicator tip 10 (FIG. 1) (and/or for releasably coupling distal end 640 of syringe 600 to proximal end 32a of base 32 of applicator tip 30), e.g., via a thread-lock engagement. However, it is also envisioned that syringe 600 be releasably engageable with applicator tips 10, 30 via any other suitable mechanism including Luer-Lock threading, snap-fitting, friction-fitting, etc.

Referring now to FIG. 7, a fluid supply assembly 700 is shown configured for use with applicator tip 10 (FIG. 1) and/or applicator tip 30 (FIG. 3). Fluid supply assembly 700 generally includes a handle, or housing 710 having a proximal end 712, a distal end 714 and at least one chamber 716 therein for retaining a fluid (or fluids). Housing 710 is coupled to an energy source 720 for supplying electrical power to fluid supply assembly 700 for dispensing fluid from fluid supply assembly 700, although it is envisioned that fluid supply assembly 700 may also be battery-powered. A conduit 730 disposed within housing 710 is coupled to chamber 716, extends distally through housing 710 and ultimately couples to connector 740 disposed at distal end 714 of housing 710. Connector 740 includes threading 742 for releasably engaging proximal ends 12a, 32a of applicator tips 10, 30 (FIGS. 1, 3, respectively) thereon, although other releasable engagement mechanisms are contemplated.

Continuing with reference to FIG. 7, housing 710 includes a pair of buttons, or controls 750, 760 for controlling the operation of fluid supply assembly 700. Controls 750, 760 may be configured to, for example, activate/deactivate the delivery of fluid from chamber 716 through connector 740 and/or for switching between various modes of operation, e.g., high-power and low-power fluid dispensing modes.

Figure 8A:
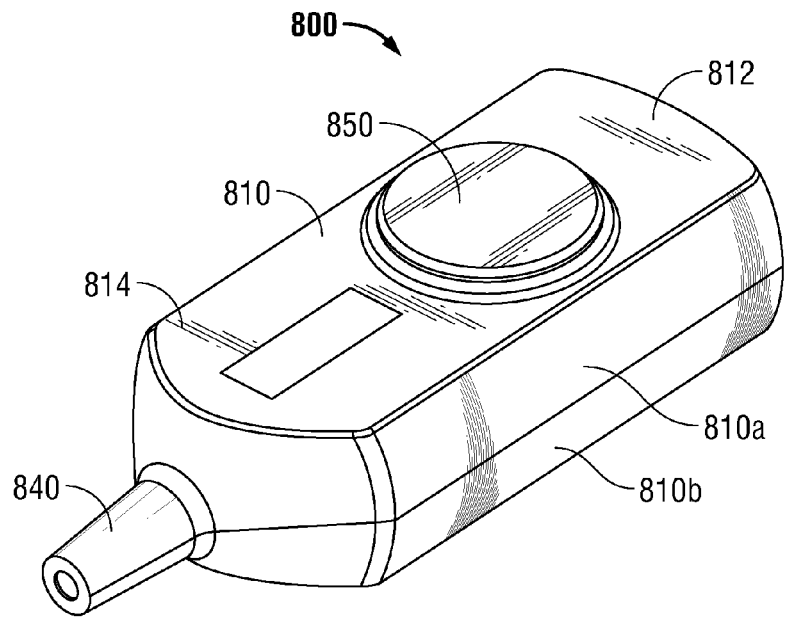
FIG. 8A is perspective view of another fluid supply assembly for use with the the applicator tip of FIG. 1 and FIG. 3.
Figure 8B:
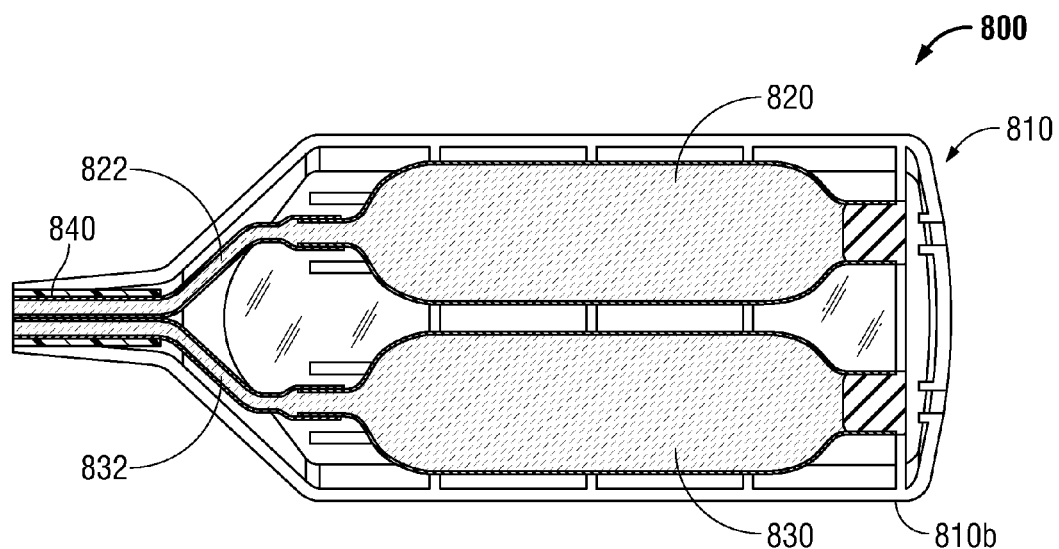
FIG. 8B is a top, cross-sectional view of the fluid supply assembly of FIG. 6A.

With reference now to FIGS. 8A and 8B, another embodiment of a fluid supply assembly, fluid supply assembly 800 is shown configured for use with applicator tip 10 (FIG. 1) and/or applicator tip 30 (FIG. 3). Fluid supply assembly 800 includes a housing 810 having a proximal end 812 and a distal end 814. Housing 810 is formed from two housing sections 810a, 810b which cooperate to form housing 810. Housing sections 810a, 810b are releasably engageable, e.g., via a snap-fit engagement, for providing access to the interior of housing 810.

As best seen in FIG. 8B, a pair of fluid chambers, or reservoirs 820, 830 are disposed within housing 810. Upon disengagement of housing sections 810a, 810b, fluid reservoirs 820, 830 may be replaced and/or interchanged with new reservoirs containing the desired fluid to be applied, e.g., saline, a pre-cursor to a hydrogel, a sealant, an adhesive, or any other solution, semi-solid, or paste. Alternatively, fluid reservoirs 820, 830 may be configured as refillable reservoirs 820, 830.

With continued reference to FIGS. 8A and 8B, housing 810 further includes a connector 840 disposed at distal end 814 thereof that is configured for engaging proximal end 12a of base 12 of applicator tip 10 (FIG. 1) (and/or proximal end 32a of base 32 of applicator tip 30 (FIG. 3)). A pair of conduits 822, 832 disposed within housing 810 couple fluid reservoirs 820, 830, respectively, to bases 12, 32 of applicator tips 10, 30 (FIGS. 1, 3), respectively, such that, upon actuation, fluid from fluid reservoirs 820, 830 is urged there through into chambers 13, 33, of bases 12, 32, respectively, to mix with the mixing component 100 prior to application to the body. Housing 810 further includes a selectively depressible actuator 850 for urging fluid from fluid reservoirs 820, 830, through conduits 822, 832 and into applicator tips 10, 30 (FIGS. 1, 3, respectively).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An applicator tip for use with a fluid applicator, the applicator tip comprising:
 a base including a rotatable collar coupled thereto, the rotatable collar selectively rotatable with respect to the base to releasably threadingly engage the base to a fluid applicator at a proximal end of the base, the base including a chamber defined therein, the chamber configured for retaining a mixing component therein;
 at least one penetrable member disposed within the base, the penetrable member at least partially enclosing the chamber to retain the mixing component therein;
 a shaft extending distally from a distal end of the base, the shaft defining a longitudinal axis and having a lumen extending therethrough, the lumen of the shaft configured for passage of a fluid therethrough; and
 wherein, upon rotation of the rotatable collar with respect to the base to threadingly engage the base to the fluid applicator, the at least one penetrable member is penetrated, thereby permitting fluid to flow from the fluid applicator into the chamber such that the fluid and the mixing component form a mixture to be applied.

2. The applicator tip according to claim 1, further comprising a nozzle disposed at a distal end of the shaft, the nozzle configured for applying the mixture.

3. The applicator tip according to claim 2, wherein the nozzle is integral with the shaft.

4. The applicator tip according to claim 2, wherein the nozzle is releasably engageable with the shaft.

5. The applicator tip according to claim 1, wherein the mixing component is a biologically active compound.

6. The applicator tip according to claim 5, wherein the biologically active compound is selected from the group consisting of peptides, proteins, DNA, siRNA, growth factors, and drugs.

7. The applicator tip according to claim 1, wherein at least one static mixer is disposed within the lumen of the shaft for facilitating mixing of the fluid and the mixing component.

8. The applicator tip according to claim 7, wherein at least one of the at least one static mixer is coated with a mixing component.

9. The applicator tip according to claim 1, wherein the at least one penetrable member includes first and second penetrable members disposed at proximal and distal ends, respectively, of the chamber for sealing the mixing component within the chamber.

10. The applicator tip according to claim 1, wherein the penetrable member is a penetrable foil that seals the mixing component within the chamber.

11. The applicator tip according to claim 1, wherein the mixing component is in the form of one of a powder, a coating, a foam, and an aerogel.

12. The applicator tip according to claim 1, wherein the fluid supplied to the base from the fluid applicator is one of a saline solution, a pre-cursor to a hydrogel, a sealant, and an adhesive.

13. The applicator tip according to claim 1, wherein the base is pre-configured such that the penetrable member retains the mixing component within the chamber.

14. The applicator tip according to claim 1, wherein the applicator tip is disposable after a single use.

15. The applicator tip according to claim 1, wherein the fluid applicator is one of manually and electrically actuated.

* * * * *